United States Patent [19]

Bennett

[11] Patent Number: Plant 6,790

[45] Date of Patent: May 9, 1989

[54] MINIATURE ROSE PLANT NAMED 'HAT PIN'

[75] Inventor: Cecilia L. D. Bennett, Chula Vista, Calif.

[73] Assignee: Susan Mae O'Brien, Chula Vista, Calif.

[21] Appl. No.: 151,255

[22] Filed: Feb. 1, 1988

[51] Int. Cl.[4] ..... A01H 5/00

[52] U.S. Cl. ..... Plt./7

[58] Field of Search ..... Plt./7

*Primary Examiner*—James R. Feyrer

[57] ABSTRACT

The subject of the present disclosure is a new and distinct variety of miniature rose plant, named 'Hat Pin', which is characterized by its very small blooms (less than 20 mm in diameter when fully opened) that are pale mauve, ranging from near Pastel Mauve to near Pastel Lilac. The blooms are usually borne one to a stem on a compact plant. The bush is well-branched and produces moderate to heavy quantity of blooms.

1 Drawing Sheet

1

The present invention relates to a new and distinct variety of a hardy, dwarf, bush plant of the miniature class; the variety being primarily characterized as a mauve.

The variety is further characterized by:

Small, semi-double (15 to 20 petals) blooms, usually borne one to a stem but on occasion in sprays of 3 to 5 or more. The blooms are held very erect and well above the foliage.

It has a slight fragrance.

The plant ranges in height from 10 to 15 inches (30 to 40 cm). The canes are sturdy and erect with moderate branching and medium to heavy foliage covering. The plant is a moderate to heavy bloomer that does well either in the greenhouse or outdoors.

The plant has good growth habits, well-shaped and attractive, bearing numerous leaflets of small size.

I have found this variety to be easily asexually reproduced by cuttings.

The seed parent was Angel Face (U.S. Plant Pat. No. 2,792), and the pollen parent was Angelglo (miniature rose plant, mauve; Ernest D. Williams; introduced by Mini-Roses, 1982). It differs from its seed parent in the following ways. It is a miniature rose with a petal count of 15 to 20, and Angel Face is a floribunda with 30 or more petals per bloom. It differs from its pollen parent in the following ways. It is a light mauve with less than 20 petals and a bloom size of 20 mm or smaller when fully opened, and Angelglo is a deep mauve with 30 petals or more and a bloom size of 30 to 40 mm when fully opened.

The descriptive matter which follows pertains to roses grown and color values observed in plants and newly opened blooms in the months of March through August 1986. The plants were grown outdoors in Chula Vista, Calif., and are believed to be accurate standards for this cultivar in similar conditions of soil and climate elsewhere.

The color photograph illustrates the variety.

Referring now specifically to the new and distinct variety of miniature rose plant named 'Hat Pin', the following is a detailed description thereof in outline; all major color plate identifications being by reference to The British Colour Council Horticultural Colour Chart, except where common terms of color definition are employed.

2

Type: Hardy, compact, bushy, greenhouse or outdoor, decorative or exhibition potted plant.

Class: Miniature.

Variety Name: Hat Pin.

Flowers Borne: Usually one to a stem, but occasionally in sprays of 3 to 5 or more on erect stems with foliage well below the blooms.

Quantity of Blooms: Moderate to heavy both outdoors or greenhouse grown.

Bud:

*Peduncle.*—Variable in length (15 to 25 mm); average diameter and sturdy: ranging in color from near Scheeles Green (860/3 to 860/2 page 860) to near Lettuce Green (861/3 to 861/2 page 861) with some tinting of bronze.

*Hairs.*—None.

*Calyx.*—Same color as the peduncle.

*Opening.*—Opens well in all weather.

Bloom:

*Size when fully opened.*—Small for a miniature variety (15 to 20 mm).

*Petalage.*—Semi-double; averaging 15 to 20 petals, arranged regularly, plus petaloids (3 to 5 or more).

*Form.*—Urn-shaped progressing immediately to fully open bloom with slight reflex of the outer margins of each petal.

Petals: Fairly thick with good substance; both the upper and under surfaces of all petals have a matte finish.

*Shape.*—Outer petals are of a broad obovate form. The intermediate petals are very much like the outer petals only narrower. The inner petals are a broad lanceolate form; and the petaloids are also lanceolate form with some occasional irregularities.

Color: Newly opened flowers from plants grown outdoors (March through August 1986), Chula Vista, Calif.

*All petals.*—Upper and Under Surfaces — Ranging from near Pastel Mauve (433/3 to 433/1 page 433) to near Pastel Lilac (437/3 to 437/1 page 437).

*General color effect.*—Newly opened flowers — Pale lavender throughout with fading of the color to near white as the bloom matures, usually 3 to 5 days or longer.

*Flower longevity.*—(March through August 1986) Plant in pot 1 to 3 days from bud with sepals reflexed to fully opened bloom. Holding at fully opened with gradually fading of color for 3 to 5 days or longer. Cut blooms at living room temperature 4 to 6 days or longer.

Reproductive organs:

*Stamens.*—Arranged uniformly around the pistil.

*Filaments.*—Varying in length with shorter filaments more proximal to the pistil; pale yellow including the anthers.

*Pollen.*—Abundant.

*Pistil.*—Short and compact; pale green with pale yellow caps on the styles.

*Ovaries.*—All encased in calyx.

*Hips.*—Some.

*Seeds.*—3 to 5 or more in each hip.

*Sepals.*—Permanent; spear-shaped; open as the bloom opens, recurving against the peduncle, when the bloom is fully opened.

Foliage:

*Leaves.*—Five to seven leaflets on the average; small size for a miniature rose plant.

*Leaflets.*—Broad ovate-shaped.

*Margin.*—Very serrated with tinting of bronze, especially noticeable on the newer foliage.

*Color.*—Ranging from near Scheeles Green (860/3 to 860/2 page 860) to near Lettuce Green (861/3 to 861/2 page 861) with occasional bronzing of the margins, especially noticeable on the newer foliage. Upper surfaces have a semi-glossy finish, and the under surfaces have a matte finish of a slightly lighter shade than the upper surfaces.

*Rachis.*—Medium strength; upper surface is grooved; under surface has 1 to 3 extremely small thorns.

*Stipules.*—Varying in length from small to medium; average width; tapering auricles angled outward at about 45 degrees.

Growth:

*Habit.*—Compact and bushy; small in height for a miniature rose plant (10 to 12 inches).

*Growth.*—Compact and well-branched.

*Canes.*—Medium diameter; sturdy; held erect.

*Main stems.*—Color — Ranging from near Scheeles Green (860/3 to 860/2 page 860) to near Lettuce Green (861/3 to 861/2 page 861) with occasional tinting of bronze, especially on the newer stems.

*Thorns.*—None on the main stems or branches; 1 to 3 extremely small thorns on the under surface of the rachis; color pale yellow.

*Branches.*—Same color as main stems.

The miniature rose plant and its flowers as herein described may vary in slight detail due to climate, soil and cultural conditions under which the variety may be grown; the present description being of the variety as grown at Chula Vista, Calif.

The following is claimed:

1. A new and distinct variety of miniature rose plant, named 'Hat Pin' of hardy, dwarf, compact growth, well-branched and attractive in appearance, substantially as illustrated and described; it is further characterized by its blooms of pale mauve, ranging from near Pastel Mauve to near Pastel Lilac which are usually borne one to a stem but on occasion come in sprays of 3 to 5 or more.

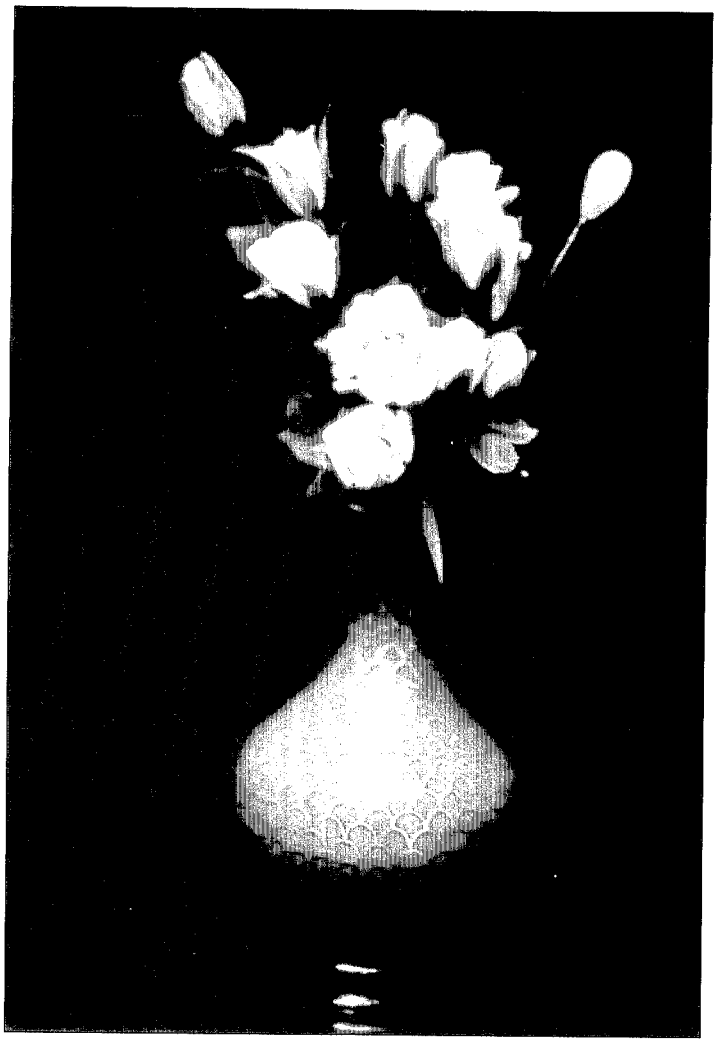

* * * * *